US008991393B2

(12) United States Patent
Jensen

(10) Patent No.: US 8,991,393 B2
(45) Date of Patent: Mar. 31, 2015

(54) MONITOR FOR MEASURING IMPROVEMENT IN INVOLUNTARY BREATHING

(76) Inventor: Steven D Jensen, South Jordan, UT (US)

(*) Notice: Subject to any disclaimer, the term of this patent is extended or adjusted under 35 U.S.C. 154(b) by 458 days.

(21) Appl. No.: 13/184,237

(22) Filed: Jul. 15, 2011

(65) Prior Publication Data

US 2011/0271959 A1 Nov. 10, 2011

Related U.S. Application Data

(63) Continuation of application No. 11/538,378, filed on Oct. 3, 2006, now Pat. No. 8,006,696.

(51) Int. Cl.
*A61M 16/00* (2006.01)
*A61M 16/06* (2006.01)
*A61M 16/14* (2006.01)
*A61M 11/00* (2006.01)

(52) U.S. Cl.
CPC .............. *A61M 16/06* (2013.01); *A61M 16/14* (2013.01); *A61M 11/00* (2013.01); *A61M 16/0683* (2013.01); *A61M 2016/0042* (2013.01); *A61M 2202/0208* (2013.01); *A61M 2230/42* (2013.01)
USPC ............ 128/204.23; 128/204.21; 128/204.22; 128/204.26

(58) Field of Classification Search
USPC ............ 128/204.23, 205.12, 205.29, 205.27, 128/206.17, 206.21, 206.28, 204.18, 128/204.21, 204.22, 204.26; 73/756, 866.5
See application file for complete search history.

(56) References Cited

U.S. PATENT DOCUMENTS

| 3,675,649 | A | * | 7/1972 | Basham et al. | ........... 128/204.22 |
| 5,857,460 | A | * | 1/1999 | Popitz | ...................... 128/206.21 |
| 6,849,049 | B2 | * | 2/2005 | Starr et al. | ..................... 600/538 |
| 6,895,962 | B2 | * | 5/2005 | Kullik et al. | ............. 128/204.18 |

* cited by examiner

*Primary Examiner* — Alireza Nia
*Assistant Examiner* — Keri J Nelson

(57) ABSTRACT

The present invention is a breathing improvement monitor that continuously measures involuntary breathing. The monitor is a sensor apparatus that is attached to a patient's mask which is connected to the monitoring apparatus. The sensor may be reusable and attachable and detachable to a mask or it may be an integral part of a breathing mask. The sensor technology may be any type sufficient in the art, including but not limited to solid state sensors, transducers, electromagnetic microturbines and the like. Since the mask does not have to be removed and the sensor provides constant signal to the monitoring apparatus, a real time status of a patient's involuntary breathing capability may be determined for a doctor's consideration.

9 Claims, 6 Drawing Sheets

MONITOR FOR MEASURING IMPROVEMENT IN INVOLUNTARY BREATHING

CROSS-REFERENCE TO RELATED APPLICATIONS

This continuation application claims the benefit of U.S. patent application Ser. No. 11/538,378, filed Oct. 3, 2006, now U.S. Pat. No. 8,006,696, the content of which is incorporated herein by reference in its entirety.

FIELD OF THE INVENTION

The present invention relates to the field of medical monitors and more particularly relates to a monitor, attachable to a breathing assistance mask, to measure improvement in involuntary breathing.

BACKGROUND OF INVENTION

There have been designed and created many devices to aid in the breathing of patients with impaired lungs. Some patients have sufficient breathing impairment such that they need a respiratory device that actually breathes for them. Others use oxygen masks and tubes that are designed only to supplement the oxygen intake for patients who have breathing impairment yet is still able to breathe on their own. Some of these devices are designed with an internal atomizer with the purpose of delivering a medication to the lungs of a patient in the form of an aerosol. A patient with impaired breathing can thus be given a constant supply of supplemental oxygen while at the same time be given life saving medications in an aerosol form through these prior art masks and tubes.

Current types of supplemental masks and tubes have no means to monitor whether any given medication has improved the breathing conditions of a patient. The current procedure to measure breathing function is with a spirometer. A spirometer is a calibrated measuring device intended to quantify the peak outward flow of air expelled from a patients lungs. A spirometer requires the use of voluntary muscle control in order to record a measurement. It not only requires that the patient understand and properly execute the instructions of a health care professional but, the procedure also requires a patient to remove their mask and breathe into a spirometer as hard as possible. The measured quantity is then supposed to correlate to the maximum breathing function. These two factors, understanding and exact execution, limit the effectiveness and reliability of a spirometer as consecutive measurements with a spirometer do not give consistent results. Young children are really at a disadvantage because they must be able to understand what is required to perform the measurement and then command their bodies to execute those requirements in the exact same manner as previous tests. Current testing also requires the patient to remove their life saving oxygen mask during measurement.

The measurement of voluntary breathing is unpredictable, especially in children. Current pulmonary measuring devices leave health care professionals to their own personal judgment and observation as to the condition of their patients with impaired breathing. Involuntary breathing, however, does not require a patient to understand and execute commands and will still show improvement, or lack thereof, when measured after treatment. As such, measurement of involuntary breathing avoids the understanding and execution of breathing tests, which are the main cause of unreliability. A breathing improvement monitor that measures involuntary breathing without requiring the patient to remove their mask or tube, thus maintaining oxygen flow, is needed to overcome the difficulties associated with the periodic measurement of voluntary breathing.

BRIEF SUMMARY OF THE INVENTION

In view of the foregoing disadvantages inherent in the known types and methods of monitoring breathing improvement, this invention provides an improved breathing improvement monitor. As such, the present invention's general purpose is to provide a new and improved breathing monitor that is capable of measuring changes in involuntary breathing while simultaneously allowing measurement without removal of a breathing assistance mask.

The present device provides a means to measure and monitor the involuntary breathing of a patient with lung impairment. The device monitors involuntary breathing and records the data in real time. The device fits into a treatment mask or tube, thus continuous monitoring and treatments can take place without removing the mask or tube. The breathing improvement monitor will allow a health care professional to monitor the breathing of a patient while medications are administered. The device will direct the health care professional to determine if a given medication or treatment is effective and whether multiple treatments are necessary, thus avoiding an unnecessary overdose and any ineffective medications.

The more important features of the invention have thus been outlined in order that the more detailed description that follows may be better understood and in order that the present contribution to the art may better be appreciated. Additional features of the invention will be described hereinafter and will form the subject matter of the claims that follow.

Many objects of this invention will appear from the following description and appended claims, reference being made to the accompanying drawings forming a part of this specification wherein like reference characters designate corresponding parts in the several views.

Before explaining at least one embodiment of the invention in detail, it is to be understood that the invention is not limited in its application to the details of construction and the arrangements of the components set forth in the following description or illustrated in the drawings. The invention is capable of other embodiments and of being practiced and carried out in various ways. Also, it is to be understood that the phraseology and terminology employed herein are for the purpose of description and should not be regarded as limiting.

As such, those skilled in the art will appreciate that the conception, upon which this disclosure is based, may readily be utilized as a basis for the designing of other structures, methods and systems for carrying out the several purposes of the present invention. It is important, therefore, that the claims be regarded as including such equivalent constructions insofar as they do not depart from the spirit and scope of the present invention.

DETAILED DESCRIPTION OF THE INVENTION

Figure 1:
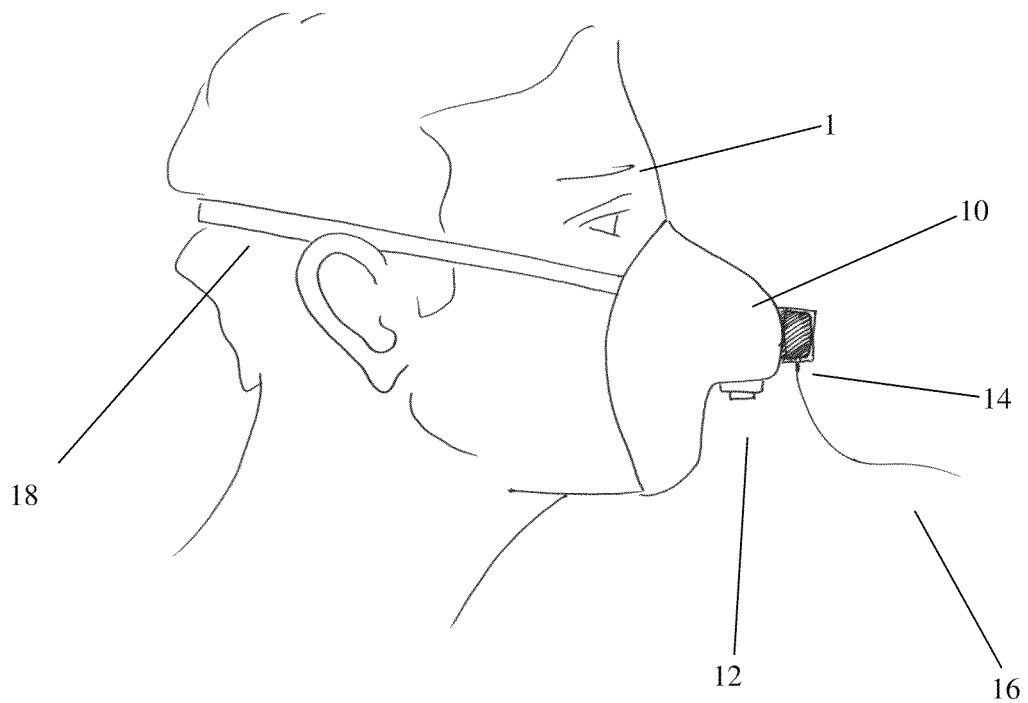
FIG. 1 is a plan view of an oxygen mask, with the present invention installed, on a patient.
Figure 2:
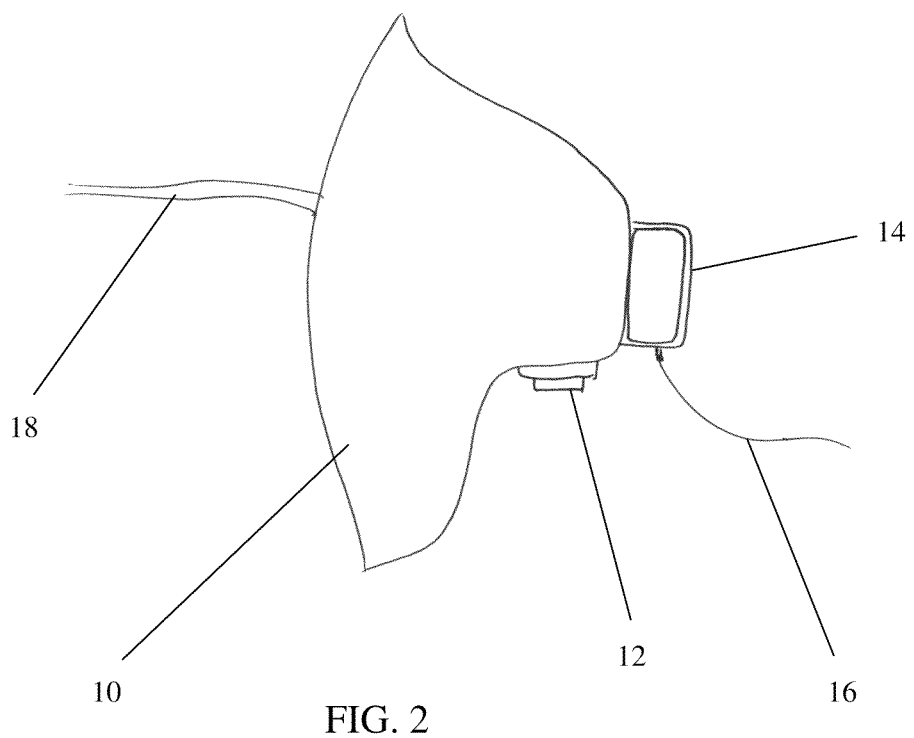
FIG. 2 is a plan view of the mask of FIG. 1 off of a patient.
Figure 3:
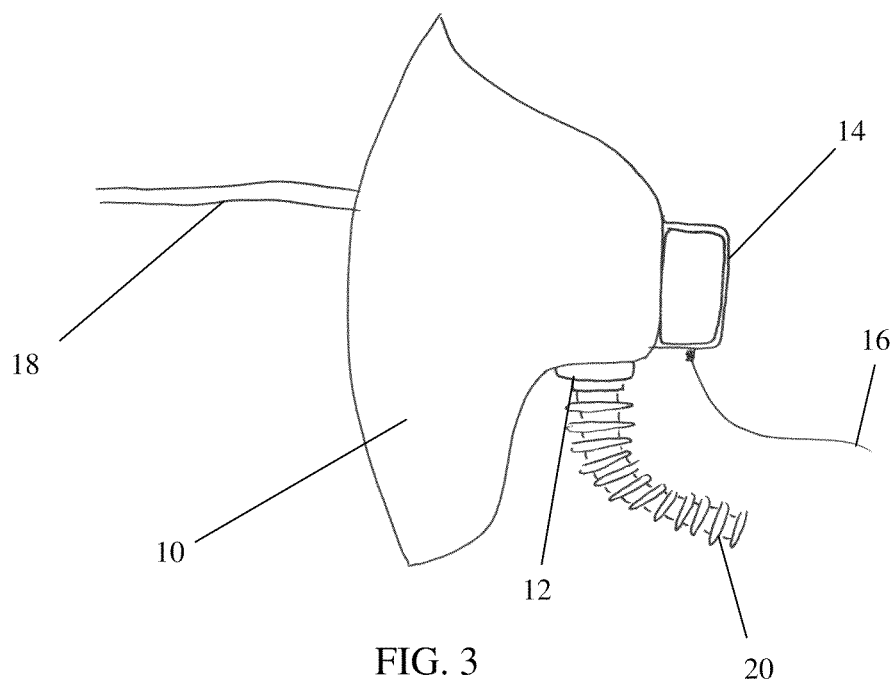
FIG. 3 is a plan view of the mask of FIG. 2 with an oxygen supply attached.
Figure 4:
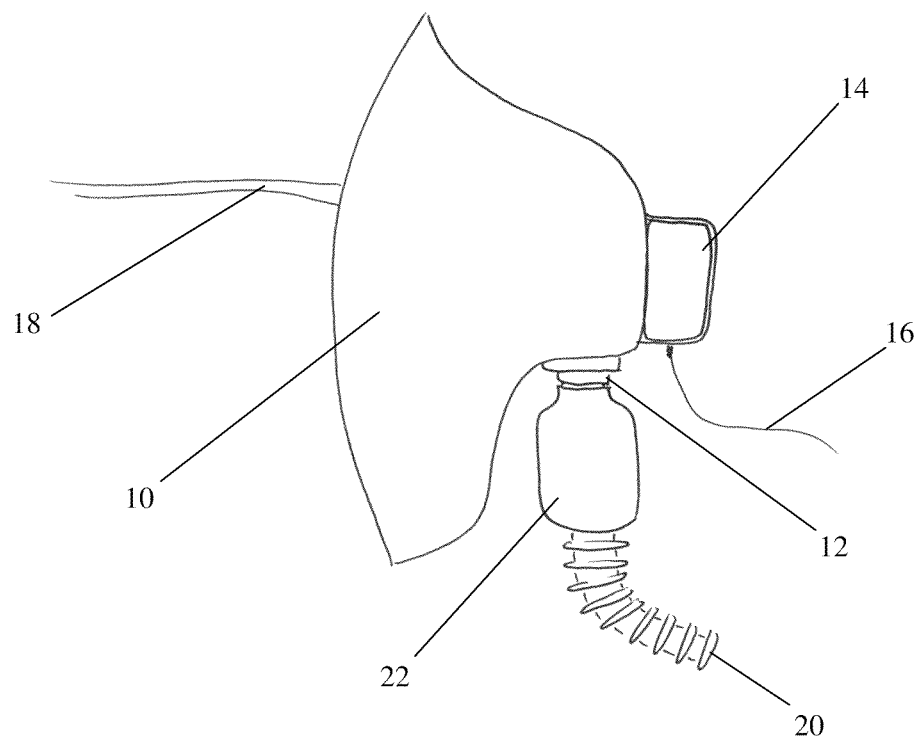
FIG. 4 is a plan view of the mask of FIG. 2 with both an oxygen supply and an in-line atomizer attached.
Figure 5:
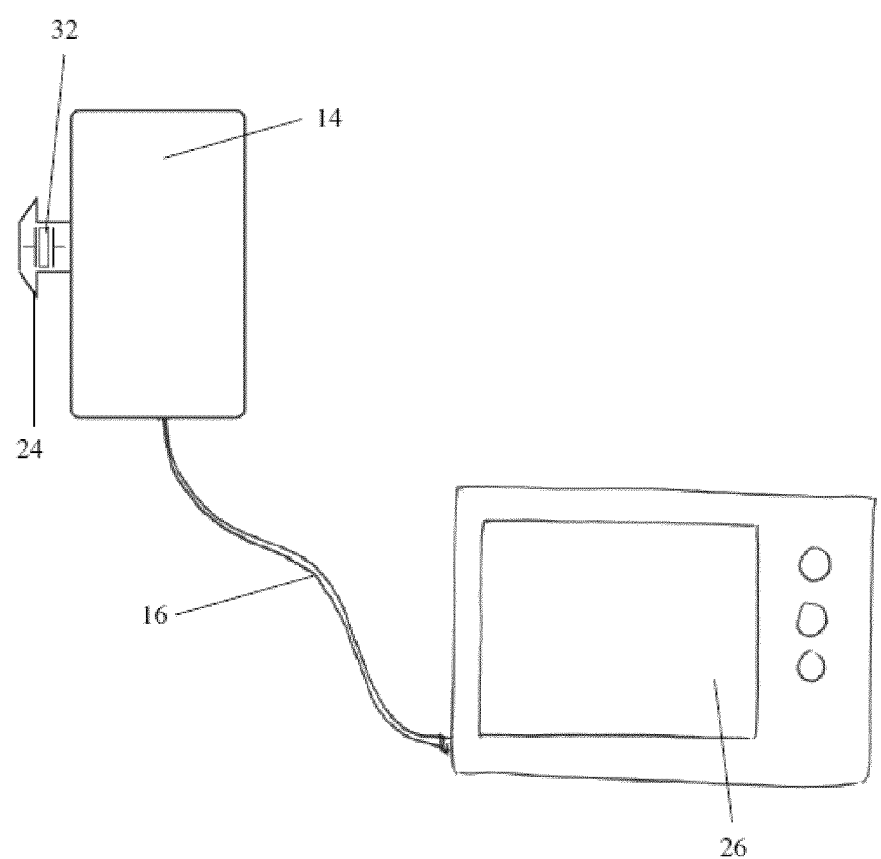
FIG. 5 is a plan view of the sensor and monitor system according to the present invention.

With reference now to the drawings, the preferred embodiment of the devices is herein described. It should be noted that the articles "a", "an" and "the", as used in this specification, include plural referents unless the content clearly dictates otherwise. As shown in FIGS. 1 and 5, the monitor according to the present invention comprises a breathing sensor 14 that is inserted into the mask 10 of a patient 1 and is operably connected 16 to a monitor 26. A standard oxygen mask 10, shown in FIG. 2, has means for securing the mask 10 on the patient 18 and an inlet 12 for oxygen connection. Oxygen is usually delivered through a tube 20 (shown in FIG. 3) attached to the inlet 12. Often, medication is introduced into the oxygen flow through an atomizer 22, shown in FIG. 4, connected in line with the inlet 12 and tube 20.

The breathing improvement monitor is designed to constantly measure the ratio of the pulmonary flow to the respiration rate as a function of time. The gathered data is displayed in real time on monitor 26 and any improvements are measured while the patient receives supplemental oxygen and medications. While shown in the figures as being connected to the mask 10, it is important to note that the sensor 14 may also be introduced into the oxygen flow at any point either in or between the tube 20 and the mask 10. The breathing improvement monitor may be a calibrated unit, measuring precise units or it could simply measure relative improvement from a baseline established prior to administering medications. The utility of the monitor derives from the constant measuring of a patient's breathing conditions and not necessarily from how the gathered data is quantified.

Figure 6:
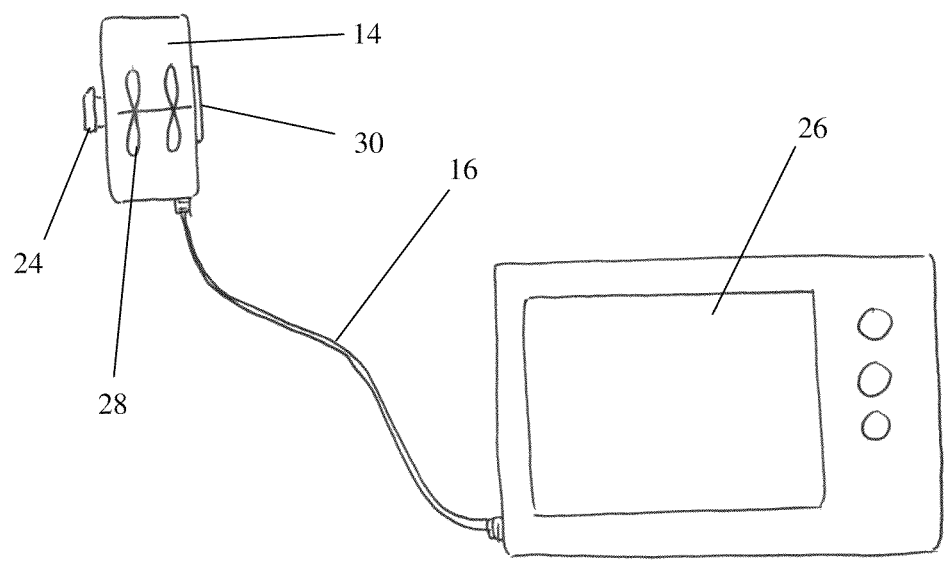
FIG. 6 is a partial section of one embodiment of the sensor system according to the present invention.

Multiple engineering approaches are possible to design and create a breathing improvement sensor 14 that is attachable to a mask 10 or tube 20. The breathing improvement sensor 14 may also be permanently attached to the mask 10 or tube 20, or configured as an attachable separate unit, as shown in FIGS. 5 and 6. It may be more cost effective to have the breathing improvement sensor attachable and reusable, so that the mask or tube becomes the only disposable piece. In the embodiment shown in FIG. 5, the sensor 14 has an attachment means, in this case a nub 24 insertable into the mask 10. Nub 24 may also contain the active measuring component of the sensor 14, such as a piezoelectric transducer, or may be hollow and allow airflow into the sensor 14 for measurement, as shown in FIG. 6.

The choice of a sensor or sensors provide multiple engineering and designing possibilities. It is conceivable to have a single sensor 14 that is capable to gather all the necessary data. Such a sensor, shown in partial section in FIG. 6, comprises a small turbine 28 that spins in response to a patient's respiration rate. The turbine 28 is connected to a DC generator 30 that generates electricity in response to the direction and speed of the turbine's motion. The respiration rate would be recorded when a patient exhales and the turbine 28 spins in one direction, producing a voltage of a given polarity and value. When the patient inhales, the turbine 28 will spin in the opposite direction producing a voltage of the opposite polarity. The change of a measured voltage of a given polarity followed by no measured voltage, then a measurement of the voltage of the opposite polarity followed by no voltage would constitute one respiration cycle. The total number of revolutions, polarity, and the total amount of power produced during the respiratory process are recorded to monitor a patient's breathing efficiency.

If oxygen were continuously running then the turbine 28 would always be spinning in the exhalation direction and the turbine 28 would only slow down during the inhalation cycle. Nevertheless, as long as there is a cyclic change in values, an algorithm can be devised to measure the breathing cycle regardless of whether there is a positive flow introduced into the mask or the patient provides all airflow.

Another appropriate sensor is a pressure sensitive diaphragm. The diaphragm compresses and decompresses during a respiration cycle. A respiration rate would be recorded when the diaphragm is compressed followed by dropping to zero state, followed by a decompression and again another zero state. The sensor would record the pressure curve throughout the entire respiration cycle and then integrate the area under this curve. The ratio of the pressure curve area to the respiration rate as per a given unit of time would provide a means to measure the breathing rate. The diaphragm may be located either inside the sensor 14 or may be mounted upon the nub 24 that is inserted within the patient's airflow.

It is also possible to construct an involuntary breathing improvement monitor using other sensors. Such sensors include but are not limited to piezoelectric and other solid state transducers. Two separate sensors gathering data separately can determine the breathing rate. A pressure sensor and a respiration rate counter, used in conjunction, can also provide meaningful data. Multiple sensors and combinations thereof exist that can be used to gather meaningful data. Again, dependant upon the type of sensor components used, the actual construction of sensor 14 will vary and such variance is still considered within the scope of this invention.

Although the present invention has been described with reference to preferred embodiments, numerous modifications and variations can be made and still the result will come within the scope of the invention. No limitation with respect to the specific embodiments disclosed herein is intended or should be inferred.

What is claimed is:

1. A breathing assistance apparatus, comprising:
   a mask capable of fitting over a mouth and nose of a patient;
   an inlet through which one or more breathing improvement medications are administered;
   a breathing sensor assembly having a nub, the nub being removably attachable to the mask;
   a pressure sensitive transducer located within the nub; and
   a monitoring system in data communication with the breathing sensor assembly;
   wherein:
      the breathing sensor assembly measures real-time changes in a patient's respiration cycle, and transmits data representing the real-time changes in a patient's respiration cycle to the monitoring system;
      the monitoring system processes the data representing the real-time changes in a patient's respiration cycle to calculate a ratio of the pulmonary flow to the respiration rate as a function of time and a displays the ratio of the pulmonary flow to the respiration rate as a function of time;
      the monitoring system records and displays the effect to the ratio of the pulmonary flow to the respiration rate as a function of time after one or more breathing improvement medications are administered; and
      the monitoring system compares a baseline ratio to a real-time ratio of pulmonary flow to a respiration rate as a function of time.

2. The breathing assistance apparatus recited in claim 1, wherein the inlet is attached to a tube that is connected to an oxygen supply, wherein the tube is configured to transport oxygen from the oxygen supply through the inlet of the mask.

3. The breathing assistance apparatus recited in claim 2, wherein the monitoring system records and displays the effect to the ratio of the pulmonary flow to the respiration rate as a function of time after oxygen is supplied through the inlet.

4. A breathing assistance apparatus, comprising:
a mask capable of fitting over a mouth and nose of a patient;
a breathing sensor assembly having a nub, the nub being removably attachable to the mask;
a pressure sensitive transducer located within the nub; and
a monitoring system in data communication with the breathing sensor assembly;
wherein:
 the breathing sensor assembly measures real-time changes in a patient's respiration cycle, and transmits data representing the real-time changes in a patient's respiration cycle to the monitoring system;
 the monitoring system processes the data representing the real-time changes in a patient's respiration cycle to calculate a ratio of the pulmonary flow to the respiration rate as a function of time;
 the monitoring system establishes a baseline ratio of the pulmonary flow to the respiration rate as a function of time, and then measures relative changes to the baseline ratio after the baseline ratio is established; and
 the monitoring system compares the baseline ratio to a real-time ratio of pulmonary flow to the respiration rate as a function of time.

5. The breathing assistance apparatus recited in claim 4, wherein the monitoring system is a calibrated unit that measures precise units.

6. A breathing assistance system, comprising:
a mask capable of fitting over a mouth and nose of a patient, the mask having an inlet located within the mask through which one or more breathing improvement medications can be administered;
a tube connected to the inlet through which the one or more breathing improvement medications are delivered to the inlet;
an atomizer connected in line with the tube to atomize the one or more breathing improvement medications;
a breathing sensor assembly having a nub, the nub being removably attachable to the mask;
a pressure sensitive transducer located within the nub; and
a monitoring system in communication with the breathing sensor assembly;
wherein:
 the breathing sensor assembly measures real-time changes in a patient's respiration cycle, and transmits data representing the real-time changes in a patient's respiration cycle to the monitoring system;
 the monitoring system processes the data representing the real-time changes in a patient's respiration cycle to calculate a ratio of the pulmonary flow to the respiration rate as a function of time;
 the monitoring system calculates the ratio of the pulmonary flow to the respiration rate as a function of time for an initial time period to establish a baseline ratio; and
 the monitoring system compares the baseline ratio to a real-time ratio of pulmonary flow to the respiration rate as a function of time.

7. The breathing assistance system recited in claim 6, wherein the monitoring system indicates the difference between the baseline ratio to the real-time ratio after one or more breathing improvement medications are administered.

8. The breathing assistance system recited in claim 7, wherein at least one of the one or more breathing improvement medications includes oxygen.

9. The breathing assistance system recited in claim 8, wherein the monitoring system also measures a calibrated unit of the ratio of pulmonary flow to the respiration rate as a function of time.

\* \* \* \* \*